United States Patent

Wolf et al.

[11] Patent Number: 5,851,489
[45] Date of Patent: Dec. 22, 1998

[54] SPECIMEN SLIDE FOR A MICROSCOPE

[75] Inventors: Bernhard Wolf, Stegen; Werner Baumann; Alfred Dumbs, both of Freiburg; Gerd Sulz, Umkirch; Ulrich Sieben, Reute, all of Germany

[73] Assignee: Micronas Intermetall GmbH, Freiburg, Germany

[21] Appl. No.: 737,688

[22] PCT Filed: May 13, 1995

[86] PCT No.: PCT/EP95/01822

§ 371 Date: Nov. 15, 1996

§ 102(e) Date: Nov. 15, 1996

[87] PCT Pub. No.: WO95/31716

PCT Pub. Date: Nov. 23, 1995

[30] Foreign Application Priority Data

May 17, 1994 [DE] Germany ............... 44 17 079.3

[51] Int. Cl.$^6$ ............................................. G01N 33/48
[52] U.S. Cl. ............................. 422/82.02; 435/288.3
[58] Field of Search ........................ 422/82.01–82.02; 435/288.3, 287.9, 305.1

[56] References Cited

U.S. PATENT DOCUMENTS

| 3,322,504 | 5/1967 | Capuano | 422/82.02 |
| 3,572,892 | 3/1971 | Metzgar et al. | |
| 4,209,299 | 6/1980 | Carlson | 422/82.02 |
| 4,974,952 | 12/1990 | Focht | 350/536 |
| 5,030,418 | 7/1991 | Miyata | 422/82.02 |
| 5,278,048 | 1/1994 | Parce | 436/27 |

FOREIGN PATENT DOCUMENTS

| 0 347 579 A2 | 12/1989 | European Pat. Off. |
| 0 545 284 A1 | 6/1993 | European Pat. Off. |
| 0 574 354 A1 | 12/1993 | European Pat. Off. |
| 3924701 A1 | 1/1991 | Germany |
| 42 36 421 A1 | 5/1994 | Germany |

OTHER PUBLICATIONS

*Clinical Chemistry, Micromachined Analyzers on a Silicon Chip*, vol. 40, No. 9, 1994, Philippe Arquint et al., pp. 1805–1809.

Primary Examiner—Lyle A. Alexander
Attorney, Agent, or Firm—Panitch Schwarze Jacobs & Nadel, P.C.

[57] ABSTRACT

A specimen slide (1) for a microscope, camera or other such observation device has a receiving area (2) for cell or tissue samples or other such organic material and a smaller observation area (3) for the organic material. The specimen slide (1) at least in the observation area is made of transparent material. Within the receiving area (2) the specimen slide (1) is provided with thin-film sensors (6 to 12) adjacent to the observation area (3) for measuring physiological parameters of the organic material. The chemical and physical characteristics of the organic material under observation can be picked up by the sensors while it is observed, for example under a microscope. Sensors of differing types can be provided, such as interdigital capacitors (6), NO sensors (8), $O_2$ sensors (9) or temperature sensors (11), thereby making available important physiological measurement and/or control parameters.

25 Claims, 3 Drawing Sheets

SPECIMEN SLIDE FOR A MICROSCOPE

BACKGROUND OF THE INVENTION

The invention relates to a specimen slide for a microscope, camera or other such observation device, having a receiving area for cell or tissue samples or other such organic material and further having a smaller observation area for the organic material. The specimen slide at least in the observation area is made of transparent material.

Specimen slides of this character have been known for a long time and enable an organic or biological substance arranged in the receiving area of the specimen slide to be simply positioned together with the specimen slide on the specimen stage of a microscope. The specimen slide is transparent at least in the receiving area in order that light can be transmitted by a light source through the substance under observation during examination with the microscope.

A drawback in this connection is, however, that the organic material under observation has to be arranged in close proximity to the objective of the microscope during examination in order to achieve a sufficient magnification factor and to avoid optical aberrations in the microscope. The organic material, which may be a cell culture for instance, is not easily accessible during examination with the microscope, with the result that it is hardly possible for additional examinations to be carried out on the cell culture of relatively short life under the microscope.

SUMMARY OF THE INVENTION

The object underlying the invention is therefore to provide a specimen slide of the character set forth at the outset, wherein an objective, an illuminating device or other such optical device can be arranged in close proximity to the receiving area and wherein nevertheless a further-reaching examination of the organic material is possible during the optical observation.

This object is accomplished in that within the receiving area, adjacent to the observation area, the specimen slide has at least one thin-film sensor or planar sensor for measuring physiological parameters.

This sensor can be of especially compact design and can be integrated in the specimen slide particularly in the planar technique. Similar to an integrated circuit, the specimen slide can therefore be mass-produced especially simply and cost-advantageously.

In an advantageous way the thin-film or planar sensor adjacent to the observation area enables a further-reaching examination of the organic material by a measuring signal parallel to the optical information obtained for example by examination with a microscope. Due to its low overall height, the sensor can be integrated in the specimen slide or arranged on the surface of the specimen slide, so that sensor and specimen slide form a unit of especial handling facility. The low overall height of the sensor also has especially favourable effects during examination with a microscope, because the objective or condenser lens of a microscope can be brought close to the organic material arranged in the receiving area of the specimen slide, without the objective or condenser lens being obstructed by the sensor. The sensor may be provided by way of example in the form of an ionic concentration sensor for measuring $H^+$, $Na^+$, $Ca^{2+}$, $K^+$ or Cl ions, an oxygen sensor, an NO sensor, a $CO_2$ sensor, a temperature sensor, an interdigital capacitor or reference electrodes. Depending on application, the specimen slide may be equipped with further sensors, particularly optical ones, such as grid couplers for example.

With the use of the specimen slide embodying the invention, important physicochemical parameters of the organic or biological material under observation are made available while at the same time it can be observed, for instance with a microscope. The specimen slide is suited particularly for monitoring and/or measuring the reaction of biological material to various external chemical (e.g. cytostatic agents, changes in ionic concentration, pharmaceuticals, environmental toxicants, washing agents), physical (e.g. temperature changes, electromagnetic fields, irradiation, acceleration) as well as biological (e.g. antigens, viruses, bacteria, changes in nutrient medium) stimuli. The specimen slide can be used both for scientific purposes and as a biosensor, for instance in water control, whereby a sample of the water under examination is brought into contact with test cells on the specimen slide and the reaction of the test cells is determined by means of the sensors and possibly by optical observation.

A further development of the invention contemplates that a plurality of sensors are distributed over the periphery of the observation area, preferably on a circle, adjacent to the observation area. In an advantageous way a specimen slide is thus provided having a plurality of mutually complementary and possibly cross-checking sensors for measurements of cellular processes. In particular, this also enables a correlation of the measured values determined by the individual sensors, for instance by producing locus diagrams, hence significantly improving the dependability of information about the organic material situated on the specimen slide. The individual sensors may be connected to an evaluating unit, for example a microcomputer, enabling an automatic evaluation or analysis, particularly of complex physiological processes. The microscopic data can also be taken into consideration if, for example, connected to the microscope is a CCD camera connected by an interface to the microcomputer and by methods of image processing the microcomputer determines suitable criteria for evaluating the microscope images.

The specimen slide is suitably provided with electric connections or contact surfaces for picking off measured values, measuring signals and/or for the power supply of the sensors. The specimen slide can then be simply connected to an external evaluating unit for temporarily storing, displaying or processing the measured values detected by the sensors. The specimen slide is easily changeable, allowing several specimen slides to be successively connected to the same evaluating unit.

It is especially advantageous if the sensors are at least partly sunk in, and are preferably flush with, the surface of the specimen slide. As a result, a flat receiving surface on which test cells or similar cell cultures can evenly spread is obtained in the receiving area of the specimen slide. This avoids any inhomogeneities in the cell culture, as are liable to occur if there are any unevenesses or a step or shoulder in the receiving area.

It is advantageous if at least one sensor takes the form of an integrated circuit with field-effect transistors. Such sensors have good sensitivity and can be inexpensively mass-produced by means of semiconductor technology. Field-effect transistors are suited particularly for an integration for cell potential measurement, whereby interdigital capacitors and further sensors (ISFET's) can be integrated on the chip.

The surface of the specimen slide is suitably provided with strip conductors which are for instance printed, vapour-deposited and/or at least partly sunk in the surface. Similarly as in a board, the sensors can then be simply connected with one another and with the contact surfaces and any other electronic components provided on the specimen slide by the strip conductors.

One embodiment of the invention proposes that the specimen slide, except for the observation area, essentially consists of silicon, that the sensors are silicon semiconductors and are integrated in the silicon of the specimen slide and that in the observation area the specimen slide consists of an optically transparent material. A specimen slide which can be mass-produced to especial advantage as far as costs are concerned is thus obtained in which a plurality of sensors, preferably all the sensors, can be integrated in a common chip. In the observation area the chip can then have an opening in which a glass window or a plastic window of biologically inert, highly transparent material, for example polycarbonate, can be inserted.

A further development of the invention proposes that for processing and/or evaluating the sensor signals, the specimen slide has a microprocessor, particularly a signal processor. The various connections for the sensors then do not need to be separately routed to the outside, but can be connected on the specimen slide by, for example, strip conductors to the microprocessor or signal processor which digitizes the measured values of the sensors and routes them to the outside by way of e.g. a serial interface accessible at respective connection contacts on the specimen slide. The specimen slide need then only have a few external connections with which all the sensors situated on the specimen slide can be addressed and/or read out. The microprocessor or signal processor also permits processing of measured values, for example filtering, correlation, smoothing or temporary storage of measured values. In addition, non-linearities of the sensors can be taken into consideration in the processor, for example heeding characteristic curves or any temperature drift.

In order that when the specimen slide is illuminated the photoelectric effect does not cause any falsification of the measured values in the semiconductors of the sensors, it is advantageous if the sensors are shielded against light and if for this purpose in particular a layer impervious to light, preferably a black layer, is provided. If the specimen slide has a chamber closure and such a light shield is provided at the upper side and at the underside of the sensors, the specimen slide is suited for measurements both on inverse and on non-inverse microscopes. Hence it is possible for examination with the microscope to be selectively carried out either on upper side of the organic material facing away from the specimen slide or on the underside, through the specimen slide.

To enable the organic material situated on the specimen slide to be kept as accurately as possible to normal temperature (37.0° C. for mammalian cells), it is advantageous if the specimen slide is temperature-regulable.

It is especially advantageous if the specimen slide has a temperature-controlled thin-film heating and if the same is preferably provided on the specimen slide at an outer surface thereof facing away from the receiving area. In the case of a specimen slide in the form of a rectangular wafer, where the receiving area is arranged on one face, the thin-film heating is hence provided on the averted face. By this means, the specimen slide and the organic material on it are heatable especially uniformly, practically throughout the face of the specimen slide. For temperature control of the thin-film heating, the specimen slide may have a temperature sensor preferably arranged within the receiving area and adjacent to the observation area.

A holder may be provided for fixing the specimen slide, for example to the specimen stage of a microscope. It is advantageous if the holder is temperature-regulable and in the position of use is connected with good thermal conductivity to the specimen slide, preferably by means of a heat-transferring surface contacting the underside of the specimen slide. The specimen slide is temperature-regulable by means of the holder and therefore it does not need any heating of its own.

For temperature-regulation of the specimen slide, the holder may have a liquid duct or a hollow wall for temperature-regulating liquid, with a liquid inlet and a liquid outlet. The liquid duct can then be connected by a circulating pump to a thermostatically controlled water bath or a water circuit, so that the cell material under observation can be kept very accurately to a predetermined temperature.

Another embodiment proposes that the holder has a thermostatically controlled electric heating. Such an electric heating can be controlled, for example, by a semiconductor temperature sensor, enabling the temperature of the holder and specimen slide connected thereto to be regulated with great accuracy.

It is advantageous if for picking off electric signals, particularly of the sensors, and/or for feeding current, a contact member which is adapted to be attached or pressed onto the contact surfaces of the specimen slide and has contacts mating the contact surfaces of the specimen slide is provided. With such a contact member, the external electric connections can be established for several sensors at a time, needing practically only the flick of the wrist.

It is especially advantageous if the specimen slide is integrated in or connected to a standardized DIL package or PLCC IC package. The IC package of the specimen slide can then be simply inserted in an IC header for electrically connecting the sensors, for instance to an external evaluating unit. The observation area of the specimen slide is preferably arranged centrally with respect to the face of the IC package in order that use can be made of the space between the contact banks of the IC header for observing and/or illuminating the organic material.

A further development of the invention proposes that the specimen slide has a chamber closure laterally tightly surrounding the receiving area of the specimen slide and therewith defining a substantially closed cultivation chamber, that the chamber closure has a viewing and/or illuminating window and at least one inlet opening and one outlet opening for a nutrient liquid. In an advantageous way, the organic material, for instance test cells, situated in the chamber can be kept vital on the specimen stage of the microscope under defined external conditions over a lengthy period, for instance longer than 10 minutes. This permits enhanced examination of dynamically changing cell processes.

Suitably it is proposed that the window is integral with the chamber closure and preferably consists of biologically inert, highly transparent plastic. The chamber closure can then be manufactured particularly simply, for example as a polycarbonate element having an approximately rectangular outer contour, with the window integrated. A plastic of good thermal conductivity is preferably used to enable enhanced temperature regulation of the organic material.

It is especially advantageous if the window is arranged in a depression provided in the upper surface of the chamber closure. In the depression a condenser lens with high aperture can then be brought close to the organic material.

It is advantageous if the chamber closure has locating recesses into which additional sensors with sensor holders can be detachably placed, preferably screwed or plugged in. Additional sensors, not provided on the specimen slide, can then be introduced into the chamber. These sensors are changeable at will so that the chamber can be equipped with the sensor configuration desired, according to application. It is especially advantageous that sensors more rarely required and not worth integrating in the specimen slide can also be used for measurement.

It is especially advantageous if thin-film sensors or planar sensors are provided on a chamber closure wall facing the chamber. The chamber can then be of especially compact design as a miniature chamber, so that even the smallest amounts of organic material suffice for measurement with the sensors. The sensors, which are arranged on the specimen slide and are preferably in direct contact with the cell material under observation or are covered by the cells, permit detection of the chemical-physical characteristics of the cell material, while the thin-film sensors or planar sensors of the chamber closure arranged in the nutrient liquid are suited particularly for measuring nutrient liquid parameters.

Suitably it is proposed that the specimen slide has running round the periphery of the receiving area a holding edge which projects upwardly and surrounds an opening extending to the receiving area, and that the chamber closure is adapted to be detachably inserted in the opening. After the chamber closure has been removed, the chamber is then easily accessible for introducing the organic material for example. A seal is provided at the periphery of the chamber closure and in the position of use bears internally against the peripheral edge, outwardly sealing the interior of the chamber.

It is advantageous if the specimen slide essentially takes the form of a rectangular wafer and if the receiving area is in provided on one face of the specimen slide. The specimen slide can then have the form of a commercially available, standard specimen slide, enabling it to be fixed in position without any difficulty using the holders provided on the specimen stages of most microscopes.

It is especially advantageous if at least one locating recess for inserting a contact member is provided on the specimen slide, preferably on the upper side thereof, adjacent to the narrow edges. In the functional position, the electrical contacts of the contact member are thereby aligned with especial accuracy to the mating contacts of the specimen slide. To prevent the contact member from being unintentionally withdrawn or released from the locating recess, an arresting coupling may also be provided between the contact member and the locating recess.

Suitably it is proposed that for cultivation of non-adherent cells the receiving area has a surface structure, particularly a lamellar or lattice structure. Non-adherent cells are then not so readily entrained or flushed away by the liquid nutrient current in the region where it flows through.

BRIEF DESCRIPTION OF VARIOUS VIEWS OF THE DRAWINGS

Exemplary embodiments of the invention will be described in greater detail below with reference to the drawings depicting on different scales and some in pronounced schematic form in FIG. 1 a plan view of the specimen slide embodying the invention, showing especially clearly the sensors arranged around the observation area and the strip conductors connecting them to the contact surfaces, in FIG. 2 a plan view of a specimen slide which is positioned in a heatable holder and has extending round the periphery of the receiving area a holding edge for a chamber closure and in FIG. 3 a longitudinal section through the specimen slide positioned in the holder, including a chamber closure and further including on either side thereof contact members inserted in locating recesses and serving for the electric connections of the sensors.

DETAILED DESCRIPTION OF THE INVENTION

Figure 1:
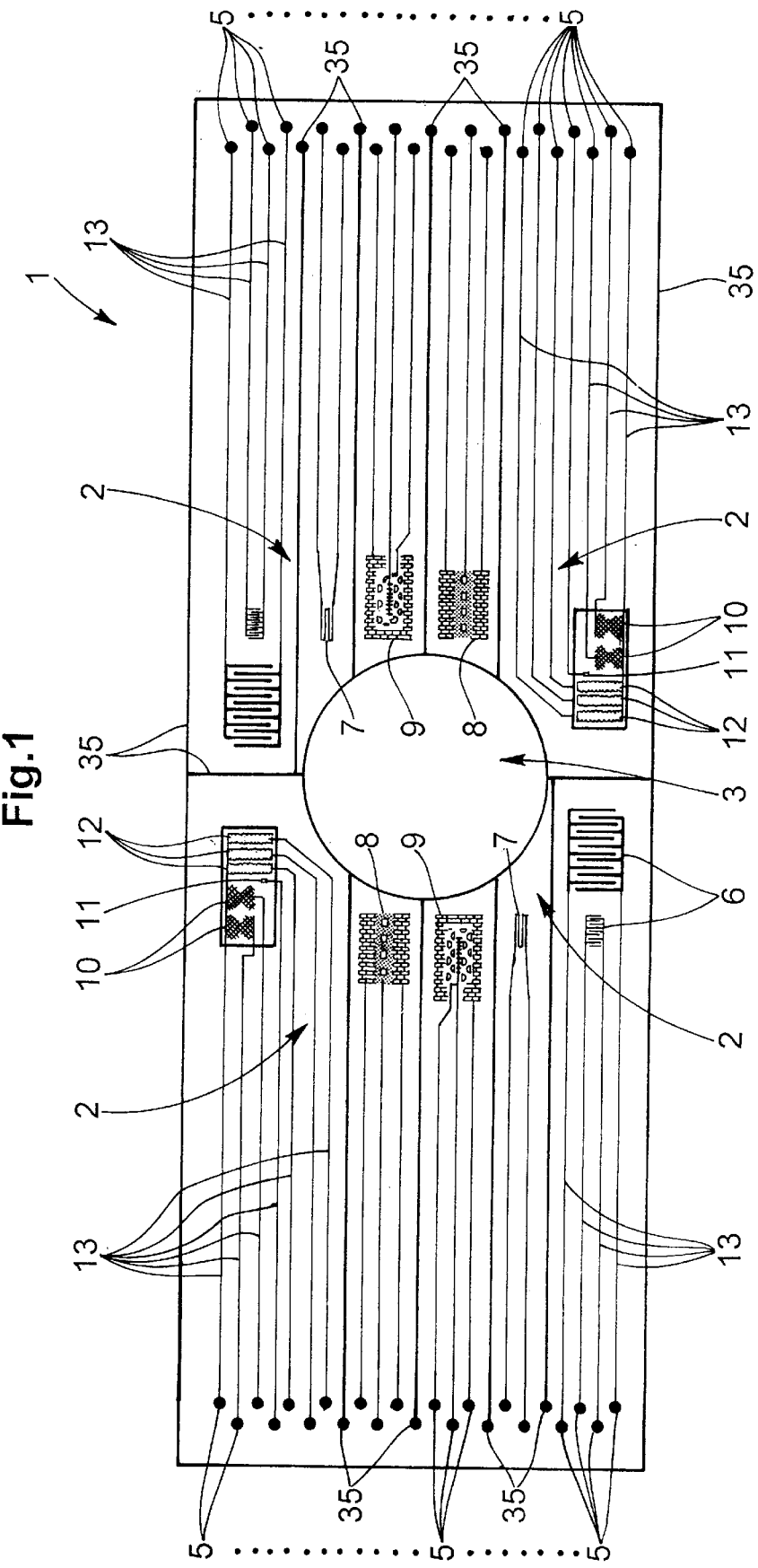

A specimen slide 1 for a microscope, a camera or other such observation device has a receiving area 2 for cell samples or other such organic material and a smaller observation area 3 for the organic material. The receiving area 2 and the observation area 3 are arranged on the upper face 4 of the specimen slide 1, the observation area 3 being formed by a circular portion of the specimen slide 1 arranged centrally with respect to the flat side 4. Within the observation area 3 the specimen slide 1 is made of highly transparent material, so that the organic material situated in the observation area 3 can be illuminated through the specimen slide 1 and/or examined with a microscope.

The specimen slide 1 has within the receiving area 2 and adjacent to the observation area 3 the following thin-film sensors: four interdigital capacitors 6, two Pt 100 thin-film temperature sensors 7, two NO sensors, two $O_2$ sensors, two cell potential sensors with FET's, two temperature sensors as well as six ISFET's. Naturally other sensor configurations are also possible, depending on use.

In an advantageous way, during the observation with a microscope, measurements of the chemical and physical characteristics of the organic material, permitting additional information to be gained on for instance cytophysiological processes in the organic material, can be carried out by the numerous sensors 6 to 12 provided on the specimen slide 1 in close proximity to or in contact with the organic material. A condenser lens of a microscope or an objective with high aperture can be arranged in close proximity to the observation area 3, without being obstructed by the sensors 6 to 12. By correlation of the measurement results gained using the various sensors and possibly by comparison with the information obtained by optical observation, the reliability of information on the state of the immobilized biological or organic cell material situated on the specimen slide 1 can be improved. The specimen slide 1 can be used both for research purposes and as a bio sensor.

The sensors 6 to 12 are at least partly sunk in, and are preferably flush with, the surface of the specimen slide 1. By this means, cell cultures on the specimen slide 1 can develop evenly throughout the receiving area 2, without being impeded by unevennesses, shoulders or steps in the receiving area 2.

The sensors 6 to 12 are of thin-film form as integrated circuits with field-effect transistors, which can be mass-produced cost-advantageously using methods of semiconductor technology.

On the specimen slide 1 are furthermore electric contact surfaces 5 for picking off measured values, measuring signals and/or for the power supply of the sensors 6 to 12. The contact surfaces 5 are arranged at the narrow edges of the upper face 4 of the specimen slide 1 and are electrically connected to the sensors 6 to 12 by strip conductors 13. The strip conductors 13 may, for instance, be printed, vapour-deposited or applied by photochemical methods to the surface of the specimen slide 1. Between the sensors 6 to 12 and around the observation area 3 are bonders 35 shielding the sensors 6 to 12.

Figure 3:
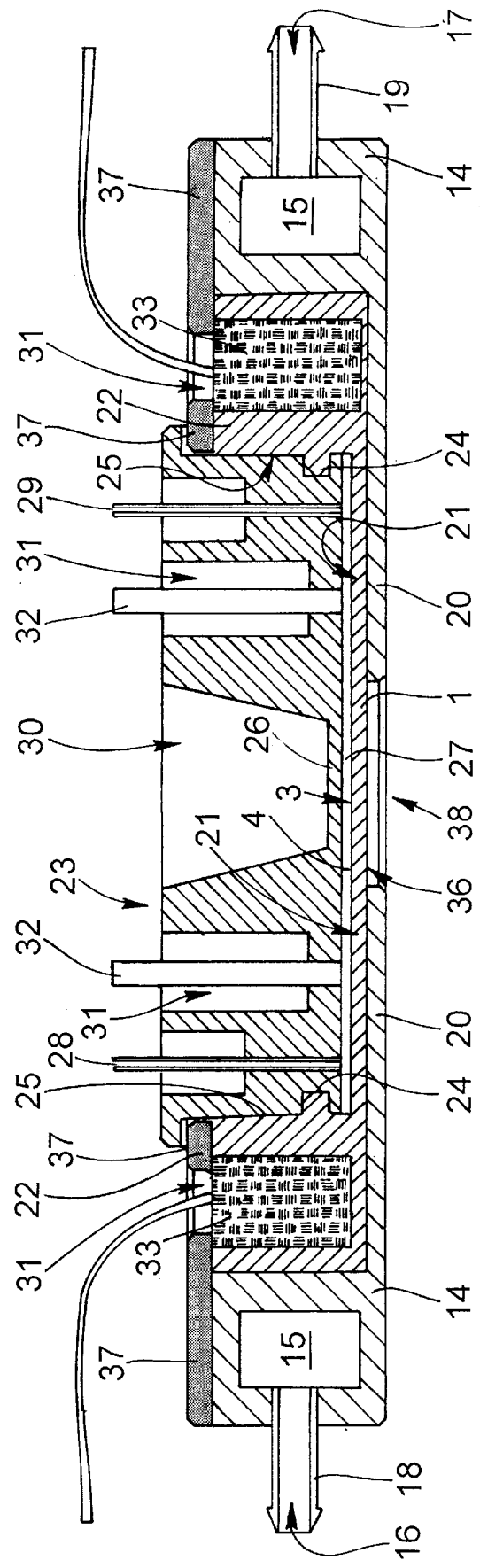

For fixing the specimen slide 1, a holder 14 is provided having a locating recess into which the specimen slide 1 can be inserted (FIG. 3). The holder 14 has extending around the outer periphery a liquid duct 15 with a liquid inlet 16 and a liquid outlet 17. The liquid inlet 16 and liquid outlet 17 have connecting branches 18 and 19, respectively, with which the liquid duct 15 is connectable to a thermostatically controlled water circuit or a temperature-regulable water bath. The holder 14 and specimen slide 1 connected thereto can thereby be temperature-regulated very accurately, so that the organic material can be kept at a practically constant temperature of, for example, 37.0° C. The holder 14 consists essentially of a corrosion-resistant material of good thermal conductivity (special steel) and has in the region of its locating recess a holding web 20 with a heat-transferring surface 21 which in the functional position bears against a major portion of the lower face 36 of the specimen slide 1 and therefore permits good heat transfer to the specimen slide 1. Beneath the observation area 3 is a circular opening 38 in the holding web 20.

Figure 2:
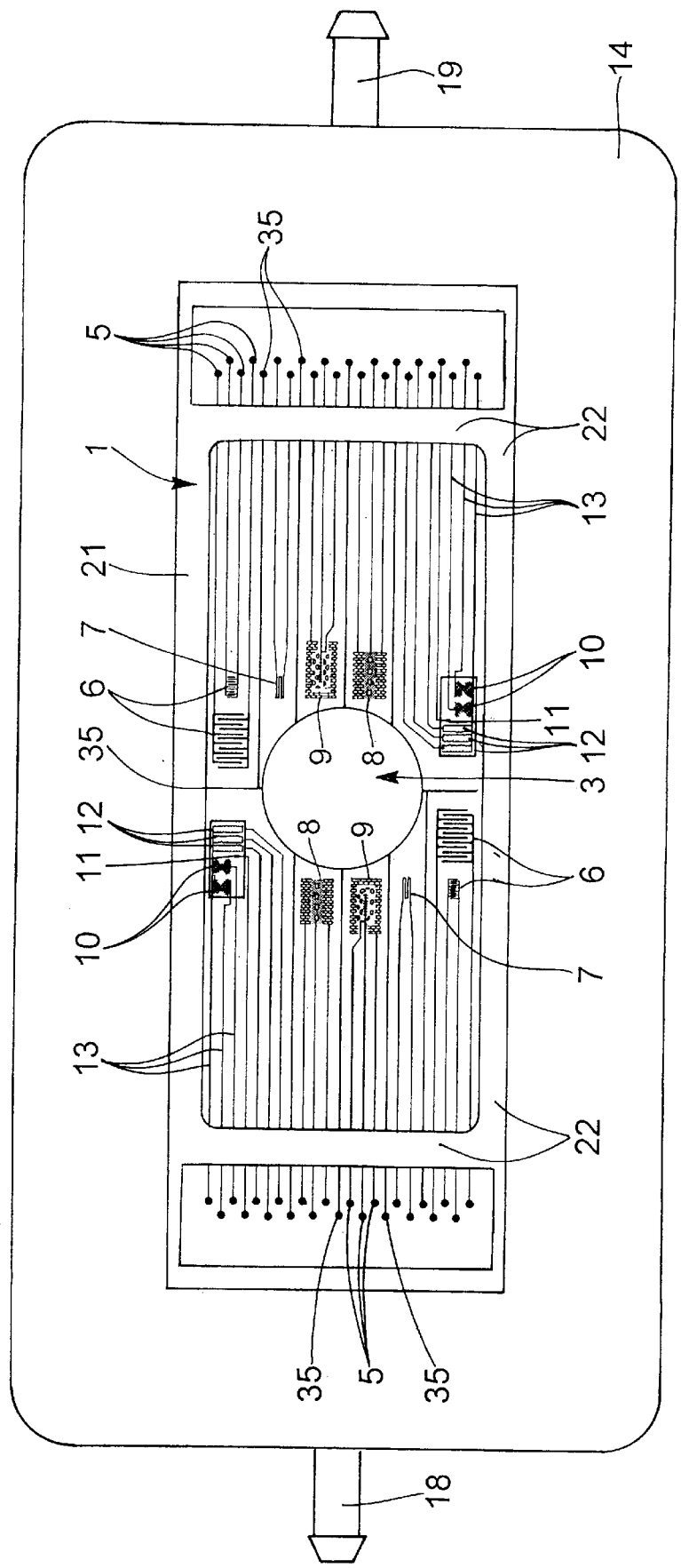

In the exemplary embodiment depicted in FIGS. 2 and 3, the specimen slide 1 has running round the periphery of the receiving area 2 a holding edge 22 projecting upwardly over the receiving area 2. The holding edge 22 surrounds an opening which extends up to the receiving area 2 and is adapted to receive a chamber closure 23. Laterally of the receiving area 2, the holding edge 22 tightly adjoins the specimen slide 1 and can take the form of a plastic frame affixed by adhesive or a moulded-on plastic component. The chamber closure 23 further has a sealing ring 24 which extends peripherally in a groove and in the functional position seals against the inner surface 25 of the holding edge 22. Therefore a substantially closed chamber volume is enclosed between the chamber closure 23 and the specimen slide 1.

The chamber closure 23 furthermore has arranged adjacent to the observation area 3 a viewing and/or illuminating window 26 through which the organic material situated in the chamber 27 can be viewed, for example with a microscope. The chamber closure 23 also has an inlet opening 28 and an outlet opening 29 for changing a nutrient liquid provided in the chamber 27. By this means, the cell or tissue material situated in the chamber 27 can be kept vital under practically constant external conditions for a longer time. Further inlet openings 28 and/or outlet openings 29 may be provided to reduce the shear forces exerted on the cells in the chamber 27 by the flow of nutrient liquid.

The window 26 is integral with the chamber closure 23 and consists of biologically inert, highly transparent plastic. The chamber closure 23 can thereby be manufactured especially cost-advantageously. The window 26 is arranged in a depression 30 inset in the upper surface of the chamber closure 23, so that a condenser lens or an objective with large aperture angle can be brought close to the cell material under observation.

The chamber closure 23 also has locating openings 31 into which additional sensors 32 with sensor holders can be detachably placed. As a result, the device composed of specimen slide 1, holding edge 22 and chamber closure 23 can be put to more versatile use, the sensor configuration being simply adaptable to the respective measuring task by changing the sensors 32 placed in the locating openings 31. Stoppers may be provided for stoppering locating openings 31 not required.

For picking off electric signals, particularly of the sensors 6 to 12 and/or for feeding current, the specimen slide 1 has two contact members 33 with contacts mating the contact surfaces 5 of the specimen slide 1.

The specimen slide 1 further has on its upper side, adjacent to its narrow ends, in each case one locating recess 34 for a contact member 33. The contact members 33 can thereby be simply positioned relative to the specimen slide 1, whereby the contact surfaces 5 of the specimen slide 1 come into contact with the mating contacts of the contact member 33. The contact members 33 have an asymmetrical cross section, preventing the contact members 33 from being inadvertently inserted in the locating openings 31 in a mirror-inverted fashion.

A cover 37 is provided on the upper side of the holder 14 and projects in some regions over the holding edge 22 and contact members 33 inserted in the locating recesses 34. The cover 37 is connectable to the holder 14 by a retaining clip (not shown), so that the specimen slide 1, contact members 33, holder 14 and cover 37 are then form-lockingly connected to form an easily portable unit.

We claim:

1. A specimen slide for a microscope, camera or other such device for observing samples of living cells, tissue or other organic material; the specimen slide (1) comprising:
   a silicon chip having a receiving area (2) for said samples,
   a smaller observation area (3) in the receiving area (2),
   an opening in the silicon chip in the observation area (3), said opening having a window (26) of optically transparent material inserted therein for visually observing the samples,
   a plurality of sensors (6 to 12) integrated into the silicon chip in the receiving area (2) and distributed around the periphery of the observation area (3),
   at least one of said sensors comprising a thin-film sensor or planer sensor for measuring physiological parameters of the samples, and
   the receiving area having a structural surface adapted for cultivation of non-adherent cells.

2. A specimen slide as claimed in claim 1, characterized in that the sensors (6 to 12) are at least partly sunk in the surface of the specimen side (1).

3. A specimen slide as claimed in claim 1, characterized in that at least one sensor (6 to 12) takes the form of an integrated circuit with field-effect transistors.

4. A specimen slide as claimed in claim 1, characterized in that the surface of the specimen slide (1) is provided with strip conductors (13) which are printed, vapour-deposited and/or at least partly sunk in the surface.

5. A specimen slide as claimed in claim 1, characterized in that the sensors (6 to 12) are shielded against light and that for this purpose a layer impervious to light is provided.

6. A specimen slide as claimed in claim 1, characterized in that the specimen slide (1) has a microprocessor for processing and/or evaluating the sensor signals.

7. A specimen slide as claimed in claim 1, characterized in that the specimen slide (1) is temperature-regulable.

8. A specimen slide as claimed in claim 1, characterized in that the specimen slide (1) has a temperature-controlled thin-film heating and that the same is preferably provided on the specimen slide (1) at an outer surface thereof facing away from the receiving area (2).

9. A specimen slide as claimed in claim 1, characterized in that the specimen slide (1) is integrated in or connected to a standardized dual-in-line integrated circuit package.

10. A specimen slide as claimed in claim 1, characterized in that the specimen slide (1) essentially takes the form of a rectangular wafer and that the receiving area (2) is provided on one face (4) of the wafer.

11. A specimen slide as claimed in claim 1, characterized in that at least one locating recess (34) for inserting a contact member is provided on the specimen slide (1) adjacent to the narrow edges.

12. A specimen slide as claimed in claim 1, characterized in that the surface structure has a lamellar or lattice structure.

13. A specimen slide as claimed in claim 1, characterized in that the specimen slide (1) is provided with electric connections or contact surfaces (5) for detecting measured values of physiological properties, for measuring signals from the sensors and/or for supplying power to the sensors (6 to 12).

14. A specimen slide as claimed in claim 13, characterized in that for detecting electric signals and/or for feeding current, a contact member (33) which is adapted to be attached or pressed onto the contact surfaces (5) of the specimen slide (1) and has contacts mating the contact surfaces (5) of the specimen slide (1) is provided.

15. A specimen slide as claimed in claim 1, characterized in that a holder (14) is provided for fixing the specimen slide (1).

16. A specimen slide as claimed in claim 15, characterized in that the holder (14) is temperature-regulable and in the position of use is connected with good thermal conductivity to the specimen slide (1).

17. A specimen slide as claimed in claim 15, characterized in that the holder (14) has a liquid duct (15) or a hollow wall for temperature-regulating liquid, with a liquid inlet (16) and a liquid outlet (17).

18. A specimen slide as claimed in claim 15, characterized in that the holder (14) has a thermostatically controlled electric heating.

19. A specimen slide as claimed in claim 1, characterized in that a chamber closure (23) is provided laterally tightly surrounding the receiving area (2) of the specimen slide (1) and therewith defining a substantially closed cultivation chamber (27), that the chamber closure (23) has a viewing and/or illuminating window (26) and at least one inlet opening (28) and at least one outlet opening (29) for a nutrient liquid.

20. A specimen slide as claimed in claim 19, characterized in that the window (26) is integral with the chamber closure (23) and of comprises biologically inert, highly transparent plastic.

21. A specimen slide as claimed in claim 19, characterized in that the window is arranged in a depression provided in the upper surface of the chamber closure (23).

22. A specimen slide as claimed in claim 19, characterized in that thin-film sensors or planar sensors are provided on a chamber closure (23) wall facing the chamber (27).

23. A specimen slide as claimed in claim 19, characterized in that the specimen slide (1) has running round the periphery of the receiving area (2) a holding edge (22) which projects upwardly and surrounds an opening extending to the receiving area (2), and that the chamber closure (23) is adapted to be detachably inserted in the opening.

24. A specimen slide as claimed in claim 19, characterized in that the chamber closure (23) has locating openings (31) into which additional sensors (32) with sensor holders can be detachably placed.

25. A specimen slide as claimed in claim 24, characterized in that stoppers are provided for closing off locating openings (31) not required.

* * * * *